(12) United States Patent
Kumar et al.

(10) Patent No.: US 8,551,748 B2
(45) Date of Patent: Oct. 8, 2013

(54) PROCESS FOR UPGRADING OF LIQUID HYDROCARBON FUELS

(75) Inventors: Manoj Kumar, Faridabad (IN); Mahendra Pratap Singh, Faridabad (IN); Maya Chakradhar, Faridabad (IN); Dheer Singh, Faridabad (IN); Veena Bansal, Faridabad (IN); Vijay Kumar Chhatwal, Faridabad (IN); Ravinder Kumar Malhotra, Faridabad (IN); Anand Kumar, Faridabad (IN)

(73) Assignee: Indian Oil Corporation Limited, Mumbai (IN)

( * ) Notice: Subject to any disclaimer, the term of this patent is extended or adjusted under 35 U.S.C. 154(b) by 557 days.

(21) Appl. No.: 12/684,390

(22) Filed: Jan. 8, 2010

(65) Prior Publication Data

US 2010/0176025 A1    Jul. 15, 2010

(30) Foreign Application Priority Data

Jan. 9, 2009   (IN) .............................. 53/MUM/2009

(51) Int. Cl.
*C12P 5/00*         (2006.01)
(52) U.S. Cl.
USPC ........................................................ 435/166
(58) Field of Classification Search
None
See application file for complete search history.

*Primary Examiner* — Tekchand Saidha
*Assistant Examiner* — Younus Meah
(74) *Attorney, Agent, or Firm* — Oblon, Spivak, McClelland, Maier & Neustadt, L.L.P.

(57) ABSTRACT

Disclosed herein a process for upgrading the liquid hydrocarbon fuels by reducing aromatic content, sulfur content and nitrogen content wherein the process comprising isolating polycyclic aromatic hydrocarbon (PAH) transforming microbes and preparing biocatalyst by mutagenesis, contacting the biocatalyst with the liquid hydrocarbon fuel in an aqueous medium for transforming the aromatic, sulfur, and nitrogen containing compounds to polar substances, subjecting the mixture of biocatalyst and the liquid hydrocarbon fuel to a process of bioconversion, removing the polar substances by liquid-liquid extraction with a polar solvent to obtain dearomatized, desulphurised and denitrogenated liquid hydrocarbon fuel and recovering the upgraded liquid hydrocarbon fuel.

14 Claims, No Drawings

PROCESS FOR UPGRADING OF LIQUID HYDROCARBON FUELS

FIELD OF THE INVENTION

This invention, in general relates to a process for upgrading liquid hydrocarbon fuels. In particular, the present invention provides a process for reducing aromatic, sulfur and nitrogen content of liquid fuel and crude oils and upgrading the same employing a biocatalyst.

BACKGROUND OF THE INVENTION

Homologous series of aromatic and heterocyclic hydrocarbons occur in varying proportions in crude oils and their refined products, depending on the source of the oil and the refining process applied. These aromatic hydrocarbons and heterocycles adversely affect several stages of petroleum production, handling, and processing. Aromatic compounds influence the persistence and toxicity of oils spilled in the environment and has poor combustion characteristics in diesel engines, including low cetane number and high particulate matter (soot) formation. During refining, nitrogen heterocycles (e.g., carbazoles) inactivate chemical catalysts, interfere with catalytic hydrodesulfurization and consume large amounts of $H_2$. As well, combustion of fuels containing S and N heteroatoms produces $SO_x$ and $NO_x$ in emissions implicated in acid rain.

Effective and cost-efficient reduction of aromatic hydrocarbons and heterocycles in crude oils and fuels therefore is desirable from an environmental viewpoint and is of interest to the refining industry.

Several chemical process have been used till date in the prior art to reduce the undesirable aromatic and heterocyclic compounds from crude oils and fuels.

U.S. Pat. No. 6,160,193 describes a two-step process for the removal of sulfur and nitrogen containing compounds from petroleum distillates. The first step of the process is to oxidize the sulfur-containing compounds of the fuel. The oxidization process converts sulfur compounds to highly polar sulfones. Nitrogen compounds are likewise converted to polar oxidized species. An example of an oxidizing agent that can be successfully used in this process is peroxysulfuric acid, often called Caro's acid. Oxidations are typically carried out at about 30 to 100° C., and preferably at 60 to 95° C. Low pressures are used, typically less than about 150 psig (pounds per square inch, gauge), and preferably less than about 30 psig, the autogenous pressures created by the vapors of the fuel and the various reactants and solvents. Sulfur- and nitrogen-containing compounds are oxidized using a selective oxidant to create compounds that can be preferentially extracted from a petroleum distillate due to their increased relative polarity. The second step of the process uses a solvent to extract the sulfones from the fuel oil.

U.S. Pat. No. 5,958,224 relates to a process for removing hard sulfurs from hydrocarbon streams by selectively oxidizing hard sulfurs in a hydrotreated stream are oxidized into the corresponding sulfoxides and sulfones, under oxidizing conditions in the presence of an effective amount of an oxidizing agent, wherein the oxidizing agent is a peroxometal complex and wherein the hard sulfurs. The said oxidizing agent is a peroxometal complex selected from the group consisting of one of the following forms: LMO $(O_2)_2$, (LL') MO $(O_2)_2$, LMO$(O_2)$.$_2$.$H_2O$, and mixtures thereof, wherein M is selected from the group consisting of Mo, W, Cr and mixtures thereof and wherein L and L' are neutral legends and wherein said sterically hindered sulfurs are converted into oxidation products.

However, the aforesaid and other thermochemical processes require high temperature; high-pressure catalytic hydrogenation to saturate and break the aromatic rings. These are not practical considering the problems posed by them including unfavorable reaction kinetics, high consumption of thermal energy and hydrogen (which contributes to greenhouse gases and other emissions), and production of less desirable side-products such as gaseous hydrocarbons through non-specific reactions.

The foregoing limitations to conventional desulfurization, denitrogenation and dearomatization process such as oxidations using chemical oxidants have spurred considerable and longstanding interest among those engaged in the extraction and refining of fossil fuels in developing commercially viable techniques of biocatalytic upgrading. Biocatalytic upgrading is as the harnessing of metabolic processes of suitable bacteria to the upgrading of fossil fuels. Biocatalytic upgrading typically involves mild (e.g., ambient) conditions, and does not involve the extremes of temperature and pressure required for HDS.

Various biocatalytic process for reduction of aromatic and heterocyclic hydrocarbons have been disclosed in the prior art.

U.S. Pat. No. 5,510,265 relates to a process for the deep desulfurization of a liquid fossil fuel containing organic sulfur comprising aromatic sulfur-bearing heterocycles, wherein the fossil fuel is (a) subjected to hydrodesulfurization or microbial desulfurization, (b) contacted with a biocatalyst in an aqueous medium in an amount and under conditions sufficient for the conversion of aromatic sulfur-bearing heterocycles to inorganic sulfur, wherein the biocatalyst comprises bacteria or a substantially cell-free preparation thereof having the capability of the parent microorganism for catalyzing the removal of sulfur from aromatic sulfur-bearing heterocycles, thereby preparing a deeply desulfurized fossil fuel; and (c) separated from the aqueous medium.

U.S. Pat. No. 5,910,440 discloses a process to remove organic sulfur from organic compounds and organic carbonaceous fuel substrates containing sulfur compounds having sulfur-carbon bonds. The steps of the process include oxidizing the sulfur species to the sulfone and/or sulfoxide form, and reacting the sulfone and/or sulfoxide form in an aqueous media of the reacting step, including a hydride transfer reducing agent. In a particular embodiment, the reducing agent is sodium formate, the oxidizing agent is a microorganism as exemplified by *Rhodococcus* species ATCC 55309 or *Rhodococcus* species ATCC 55310 or combinations thereof.

U.S. Pat. No. 5,985,650 describes a process for enhancing the rate of desulfurizing a fossil fuel containing organic sulfur compounds, comprising the steps of: a) contacting the fossil fuel with an aqueous phase containing a biocatalyst capable of cleaving carbon-sulfur bonds and a rate-enhancing amount of a flavoprotein, thereby forming a fossil fuel and aqueous phase mixture; b) maintaining the mixture of step (a) under conditions sufficient for cleavage of the carbon-sulfur bonds of the organic sulfur molecules by the biocatalyst, thereby resulting in a fossil fuel having a reduced organic sulfur content; and c) separating the fossil fuel having a reduced organic sulfur content from the resulting aqueous phase.

U.S. Pat. No. 6,071,738 relates to a process for the desulfurization of a fossil fuel containing one or more organosulfur compounds. This process comprises the steps of (1) contacting the fossil fuel with a biocatalyst capable of converting the organosulfur compound to an oxyorganosulfur compound which is separable from the fossil fuel; and (2) separating the oxyorganosulfur compound from the fossil fuel. Biocatalytic enzyme preparations that are useful in the present invention include microbial lysates, extracts, fractions, subfractions, or purified products obtained by conventional means and capable of carrying out the desired biocatalytic function. Generally, such enzyme preparations are substantially free of intact microbial cells, i.e., the enzyme preparations are cell-free fractions.

Ayala et al. 1998 (Ayala M, Tinoco R, Hernandez V, Bremauntz P, Vazquez-Duhalt (1998) Biocatalytic oxidation of fuel as an alternative to biodesulfurization. Fuel Processing Technology 57:101-111.) has described a bioxidative process for fuel desulfurization using enzyme chloroperoxidase from *Caldariomyces fumago*. The process includes the steps of biocatalytic oxidation of organosulfides and thiophenes, contained in the fuel, with hemoproteins to form sulfoxides and sulfones, followed by a distillation step in which these oxidized compounds are removed from the fuel. In this process straight-run diesel fuel containing 1.6% sulfur was biocatalytically oxidized with chloroperoxidase from *Caldariomyces fumago* in the presence of 0.25 mM hydrogen peroxide. The reaction was carried out at room temperature and the organosulfur compounds were effectively transformed to their respective sulfoxides and sulfones which were then removed by distillation. The resulting fraction after distillation contained only 0.27% sulfur. They have proposed biocatalytic oxidation of fuels as an interesting alternative to whole cell biodesulfurization.

Wu et al. (2002) (Q. Wu, M. R. Gray, M. A. Pickard, P. M. Fedorak, J. M. Foght 2002 Petroleum Chemistry Division Preprints 47(1) 615061) described biocatalytic ring opening of heterocycles dissolved in crude oil using bacterium *Pseudomonas fluoresencens* strain LP6a.

U.S. Pat. No. 7,101,410 relates to a microbiological process of desulfurization (MDS) of hydrocarbon fuels such as coal, coal tar and petroleum uses an aqueous microbial biocatalytic agent which is not significantly reproducing but is still capable of oxidizing inorganic sulfur compounds and/or of selectively cleaving sulfur-carbon bonds in organic compounds, thereby removing sulfur with insignificant losses in fuel value. Microorganisms are selected according to the type of fuel sulfur present and the environment in which the desulfurizing process is to take place. One embodiment allows droplets of highly concentrated cell-water suspensions to pass from the top surface of the fuel through to the bottom, desulfurizing along the way and removing the sulfur products of the process as well.

U.S. Pat. No. 6,461,859 relates to a process of removing thiophenic and organosulfide compounds from a fossil fuel comprising the steps of contacting the fossil fuel with hemoproteins, which oxidize the sulfur containing compounds to sulfoxides and sulfones in a reaction system containing organic solvent or not, and followed by a distillation step in which sulfoxides and sulfones are removed from the fuel. Preferred biocatalysts include hemoproteins such as chloroperoxidase from *Caldariomyces fumago*, and peroxidases and cytochromes from animal, plant or microbial cells. The hemoprotein biocatalyst can be contacted with the fossil fuel in free or immobilized forms. The reaction can be carried out in the presence of the fuel alone or with addition of any organic solvent. The biocatalytically oxidized fuel is then distilled in order to eliminate the heavy fraction which contains most of oxidized organosulfur compounds. The light distillate contains significantly lower concentrations of sulfur when compared with the starting fossil fuel.

U.S. Pat. No. 6,071,738 relates to a process for the desulfurization of a fossil fuel containing one or more organosulfur compounds. In one embodiment, the process comprises the steps of (1) contacting the fossil fuel with a biocatalyst capable of converting the organosulfur compound to an oxyorganosulfur compound which is separable from the fossil fuel; and (2) separating the oxyorganosulfur compound from the fossil fuel. The oxyorganosulfur compound can then be isolated, discarded or further processed, for example, via desulfurization by a biocatalyzed process or an abiotic process, such as hydrodesulfurization.

U.S. Pat. No. 6,943,006 relates to a process for selective cleavage of C—N bonds genes that encode for at least one enzyme suitable for conversion of carbazole to 2-aminobiphenyl-2,3-diol are combined with a gene encoding an amidase suitable for selectively cleaving a C—N bond in 2-aminobiphenyl-2,3-diol, forming an operon that encodes for cleavage of both C—N bonds of said carbazole. The operon is inserted into a host culture which, in turn, is contacted with the carbazole, resulting in selective cleavage of both C—N bonds of the carbazole. Also disclosed is a new microorganism that expresses a carbazole degradation trait constitutively and a process for degrading carbazole employing this microorganism.

U.S. Pat. No. 6,124,130 relates to a process for removal of sulfur from fossil fuels containing sulfur by incubation of the fuel with microbes isolated and purified from soil or water that selectively extract the sulfur without apparently utilizing the fuel as a carbon or energy source. Preferred biodesulfurization microbes remove at least about 20% of the sulfur. The microbes are obtained in a multi-step screen that first selects microorganisms that utilize dibenzothiophene (DBT) as a sole source of sulfur, and then tests these in incubations with fossil fuels; organisms that desulfurize DBT without metabolizing the DBT phenyl ring structures and desulfurize fuels only when a second carbon source devoid of sulfur is present are identified and employed in desulfurization processes. Two cultures, CDT-4 and CDT-4-b, were particularly efficacious in the desulfurization of liquid fossil fuels.

U.S. Pat. No. 6,071,738 relates to a process for the desulfurization of a fossil fuel containing one or more organosulfur compounds. In one embodiment, the process comprises the steps of (1) contacting the fossil fuel with a biocatalyst capable of converting the organosulfur compound to an oxyorganosulfur compound which is separable from the fossil fuel; and (2) separating the oxyorganosulfur compound from the fossil fuel. The oxyorganosulfur compound can then be isolated, discarded or further processed, for example, via desulfurization by a biocatalyzed process or an abiotic process, such as hydrodesulfurization.

US 20030170874 relates to process for treating liquid hydrocarbon, includes the steps of providing a liquid hydrocarbon containing complex sulfur-containing compounds, providing a bioactive material selected from or derived from members of genus *Alcaligenes*; and exposing the liquid hydrocarbon to the bioactive material under effective conditions such that the bioactive material interacts with the complex sulfur compounds and transforms the organic sulfur-containing compounds into inorganic sulfur compounds.

Further, several microbes are known to have activity against PAH and heterocycles especially aromatic ring opening and hydroxylation activity. U.S. Pat. No. 6,221,651 discusses a mutant *Pseudomonas ayucida* strain ATCC PTA-806 which is able to selectively cleave organic C—N bonds and reduce the nitrogen content of organic carbonaceous materials.

Considering the aforesaid prior arts, wherein the process involves numerous steps and are uneconomical even, it is desirable to provide a process capable of removing sulfur, nitrogen and reducing aromatics in one step from hydrocarbon fuels, which could be implemented without complex and costly equipment or the use of expensive or hazardous chemicals. Further, economic analyses indicate that one limitation in the commercialization of the technology is improving the reaction rates and specific activities of the biocatalysts, such as the bacteria and enzymes that are involved in the desulfurization reactions. Yet no microorganism is wild or genetically modified which can meet the activity required for commercial utilization of the process. Moreover, none of the biocatalyst is known which can attack on both organ sulfur compounds and organonitrogen compounds and reduce total aromatic content as well.

It is especially desirable if these criteria could be met to produce a fuel, which could be burnt without requiring the aqueous phase be removed prior to combustion. This need grows progressively more urgent as lower-grade, higher-sulfur fossil fuels are increasingly being used, while concurrently the sulfur emission standards set up by the regulatory authorities have become ever more stringent.

Therefore, there is a need to improve upon the limitations in the prior art. In view of the above the present invention provides an improved process for upgrading crude oil and liquid fuel by reducing aromatic, sulfur and nitrogen contents.

SUMMARY OF THE INVENTION

It is a principal object of the present invention to provide a process for reducing aromatic contents, sulfur contents and nitrogen contents in crude oil and liquid fuel by employing action of a biocatalyst.

Further object of the present invention is to provide the bioactive material comprising the biocatalyst wherein the biocatalyst oxidizes the aromatics and heterocyclic aromatics in one or multiple stages.

Yet another object of the present invention is to provide a process for preparation of the said biocatalyst using selective biological materials enabling said biocatalyst to reduce aromatic contents, sulfur contents and nitrogen contents in crude oil and liquid fuel.

Yet another object of the present invention to provide biocatalyst for reducing aromatic contents, sulfur contents and nitrogen contents in crude oil and liquid fuel by employing action of a biocatalyst, wherein said biocatalyst is recovered and employed in at least one additional stage.

The above and other objects are attained in accordance with the present invention wherein there is provided following embodiments, however the described embodiments hereinafter are in accordance with the best mode of practice and the invention is not restricted to the particular embodiments.

In accordance with one embodiment of the present invention, there is provided a process for reducing aromatic content, sulfur content and nitrogen content wherein the said process comprises of isolating polycyclic aromatic hydrocarbon (PAH) transforming microbes and preparing biocatalyst by mutagenesis, contacting the biocatalyst with the liquid hydrocarbon fuel in an aqueous medium for transforming the aromatic, sulfur, and nitrogen containing compounds to polar substances, subjecting the resultant mixture of biocatalyst and the liquid hydrocarbon fuel to a process of bioconversion, removing the polar substances by liquid-liquid extraction with a polar solvent to obtain dearomatized, desulphurised and denitrogenated liquid hydrocarbon fuel and recovering the upgraded liquid hydrocarbon fuel.

In accordance with another embodiment of the present invention, there is provided a process for reducing aromatic content, sulfur content and nitrogen content wherein the biocatalyst is contacted in amount and conditions sufficient for transforming the aromatic sulfur-bearing heterocycles, organonitrogen compounds and aromatics.

In accordance with one other embodiment of the present invention, the biocatalyst transforms aromatics, polycyclicaromatics, organosulfur compounds, organonitrogen compounds by adding polarity without degrading them.

In accordance with yet another embodiment of the present invention, there is provided a process for reducing aromatic content, sulfur content and nitrogen content wherein the organic material is contacted with biocatalyst in an aqueous media.

In accordance with still another embodiment of the present invention, there is provided a process for reducing aromatic content, sulfur content and nitrogen content wherein the organic material is treated with biocatalyst in single step or treated sequentially in which treated oil of first step is treated with same or different biocatalyst.

In accordance with still another embodiment of the present invention, there is provided a process for reducing aromatic content, sulfur content and nitrogen content wherein the biocatalyst is recovered and employed in at least one additional stage.

In accordance with yet another embodiment of the present invention, there is provided a process for reducing aromatic content, sulfur content and nitrogen content wherein the biotreated stream was recovered from the emulsion through the conventional oil water separation process like centrifugation, demulsification or any other suitable process.

In accordance with the present invention, there is provided a process for reducing aromatic content, sulfur content and nitrogen content wherein the liquid hydrocarbon fuel obtained has further reduced content of sulfur, nitrogen and aromatics.

DETAILED DESCRIPTION OF THE INVENTION

While this specification concludes with claims particularly pointing out and distinctly claiming that, which is regarded as the invention, it is anticipated that the invention can be more readily understood through reading the following detailed description of the invention and study of the included examples.

The present invention provides a process for reducing aromatic content, sulfur content and nitrogen content of liquid hydrocarbon fuel, through the action of a biocatalyst, comprising:

a. isolating polycyclic aromatic hydrocarbon (PAH) transforming microbes and preparing biocatalyst by mutagenesis;

b contacting the biocatalyst with the liquid hydrocarbon fuel in an aqueous medium for transforming the aromatic, sulfur, and nitrogen containing compounds to polar substances;

c. subjecting the mixture of biocatalyst and the liquid hydrocarbon fuel to a process of bioconversion;

d. removing the polar substances by liquid-liquid extraction with a polar solvent to obtain dearomatized, desulphurised and denitrogenated liquid hydrocarbon fuel; and e. recovering the upgraded liquid hydrocarbon fuel.

According to the present invention, the degradation of aromatics and heterocycles can be stopped at an intermediate stage and that the intermediate metabolite can be removed from the desired fossil fuel by exploiting the physical and chemical properties of the intermediate. (Aromatic in the present invention means substituted and unsubstituted monoaromatics, diaromatics, triaromatics and polycyclic aromatics.) The intermediate metabolite can be recovered and discarded or further processed, for example, via a biocatalytic or physico-chemical process, into specialty chemicals.

These oxidized metabolites can be more polar than the organosulfur, organonitrogen and aromatic compounds. In which case the metabolite can exhibit enhanced solubility in polar solvents, such as water, compared to the parent compound. The intermediate can, thus, be removed from the fossil fuel by contacting the fossil fuel with a polar solvent, which is immiscible with oil, such as an aqueous phase. Alternatively if, the organosulfur metabolite is not appreciably soluble in a polar solvent, but can be extracted into a polar solvent in which is dissolved an agent, for example, a metal salt, which reacts with the organosulfur metabolite to form a complex, which is soluble in the polar solvent.

The liquid hydrocarbon fuel according to present invention is an organic material selected from the group consisting of single and/or multi-ring aromatic compounds and alkylaromatic compounds, and their heteroatom-containing analogues, crude oil, petroleum, petrochemical streams, liquid fuels, light gas oil, light cycle oil, vacuum gas oil, diesel, gasoline, shale oils, heavy oils bitumens coal liquids and similar petroleum products, through the biochemical conversion of the aromatics, organosulfur compounds, and organonitrogen compounds present the oil by a addition of a biocatalyst which can be any microorganism living or dead, cell cultures, immobilized cell masses, mutants, fragmented cells, cell extracts, enzyme mixtures, synthetically-prepared copies of active enzyme sequences or components, and mixtures of these. In accordance with the present invention, there is provided a process for reducing aromatic content, sulfur content and nitrogen content wherein the organic material is treated with biocatalyst in single step or treated sequentially in which treated oil of first step is treated with same or different biocatalyst According to the present invention, the first stage, without carbon loss, oxidation and oxidation/ring opening of the aromatic compounds by oxidative enzymatic reactions is achieved by pre-grown whole cell biocatalysts or their enzyme extract.

The process described in the present invention, herein does not degrade the organosulfur, aromatics but transforms them in oxidized and/or ring opened metabolites compounds in presence of biocatalyst which can be isolated and used or further processed, for example, via desulfurization by a biocatalyzed process or an abiotic process, such as hydrodesulfurization.

According to the process of the present invention, the liquid fossil fuel containing aromatics and heterocycles is combined with the biocatalyst preparation.

In accordance with the present invention, there is provided a process for reducing aromatic content, sulfur content and nitrogen content wherein the biocatalyst is capable of transforming aromatics, polycyclic aromatics, organosulfur compounds, organonitrogen to polar compounds by not attacking aliphatic hydrocarbon are selected from the a group comprising, but not limited so, bacteria, fungi, their lysate, fraction, extract, sub-fraction, immobilized cells, mutants, enzyme and/or combinations thereof.

According to the present invention, a biocatalyst is provided that is adopted for bioconversion of oil to convert them to upgraded oil. The biocatalyst involves herein at least a bacteria or its enzymatic extracts, a consortium of bacteria or their enzymatic extracts, selected from the group *Pseudomonas*, *Comomonas*, and *Bacillus*.

In accordance with the present invention, there is provided a process for reducing aromatic content, sulfur content and nitrogen content wherein the biocatalyst is selected from *Psudomonas, Comomonas* and *Bacillus* sps that are naphthalene positive, phenanthrene positive, pyrene positive, benzo alpha pyrene positive, DBT positive, 4,6 DMDBT positive, hexadecane negative, indole positive, carbazole positive, anthracene positive.

According to the present invention, the biocatalysts suitable for use herein selectively oxidize: sulfur-bearing heterocycles by addition of oxygen atoms to it, nitrogen-bearing heterocycles by addition of oxygen atoms to it and aromatics including monocyclic, dicyclic and polycyclic aromatics and/or ring opening of the same and accumulating the transformed compounds.

The biocatalyst disclosed herein are capable of selectively increasing the polarity of organosulfur compounds, organonitrogen compounds adding oxygen and reducing aromatic content by opening the ring or oxidizing. While a mixture of biocatalyst can be employed, to act on inorganic and organic sulfur with the modest utilization of carbon, the more preferred agents do not substantially affect the heating value of the fuel, but selectively oxidize organic sulfur and organonitrogen compounds, which can be physically removed by extraction with polar solvent. Any of the organisms effective for reacting with the sulfur content of bitumen can be employed.

The biocatalyst used herein according to the present invention is in free or immobilized form and recovered and employed in at least one additional stage.

According to the present invention the microorganisms can function as a biocatalyst because each produce one or more enzymes (protein biocatalysts) that carry out the specific chemical reaction(s). Mutational or genetically engineered derivatives of any of these microorganisms can also be used as the biocatalyst herein, provided that appropriate biocatalytic function is retained.

Microorganisms suitable for use as the biocatalyst in present process can be derived from naturally occurring microorganisms by known techniques. These processes involve culturing preparations of microorganisms obtained from natural sources such as sewage sludge, petroleum refinery wastewater, garden soil, or coal tar-contaminated soil under selective culture conditions; exposing the microbial preparation to chemical or physical mutagens; or a combination of these processes according the known art. The process to obtain the biocatalyst is detailed as following:

Retrieving the Bioactive Material: Many different bacterial strains can be isolated that degrade a wide range of aromatic compound, ranging from 1-5 ring through a dioxygenase type of catabolic pathway by enrichment techniques. The bacterial strains were isolated by the enrichment culture technique from oil-contaminated soil. A few grams of soil were inoculated into 100 ml of minimal salt medium (MSM) containing (g/l) $Na_2HPO_4$-6.0; $KH_2PO_4$-3.0; $NH_4Cl$-1.0; $NaCl$-0.5; $MgSO_4$-0.1 and 2.5 ml of trace element solution (pH 7.0). Trace elements in the solution contained (mg/l) $MnCl_2.2H_2O$-23; $MnCl_4.H_2O$-30; $H_3BO_3$-31; $CoCl_2.6H_2O$-36; $CuCl_2.2H_2O$-10; $NiCl_2.6H_2O$-20; $Na_2MoO_4.2H_2O$-30 and $ZnCl_2$-50. A mixture of PAHs containing dibenzothiophene, carbazole and phenanthrene (200 ppm w/v, each) was used as carbon source and incubated at 30° C. on a rotary shaker (200 rpm). After one-week, 1 ml of the culture was transferred to fresh media containing crude oil (2%, $wv^{-1}$) and re-incubated for another week. Following five cycles of such enrichment, 1 ml of the culture was diluted and plated on MSM agar plates containing oily sludge as sole carbon source. The bacterial colonies obtained were further purified by streaking on Luria-Bertani (LB) agar. The ability of the isolate to utilize crude oil, kerosene, diesel, gas oil, alkanes and various PAHs as sole source of carbon and energy was assessed by inoculating it into a 24 well micro-titer plate containing 500 µl of MSM in each well and 0.2% (w/v) of test hydrocarbon as sole carbon source. The catabolic pathway may be determined studying the growth ability of the microbes on various substrates and metabolites of di-oxygenase pathway and using various specific PCR primers available in the prior art. The potential microbes can be further modified by blocking the expression of genes like extradiol dioxygenase, isomerase and hydratase aldolase by chemical mutagenesis, transposon mediated mutagenesis or gene inactivation by the process as known in prior art for the purpose. A strain mutated at particular enzyme would cause accumulation of metabolites resulting due to its activity and the degradation of PAH would terminate after that step. The ability of mutants to accumulate various metabolites was studied using dibenzothiophene as substrate because (in contrast to other PAH) its ring cleavage products are highly colored giving a rapid visual indication of substrate transformation. The products formed by mutants were confirmed by UV-spectroscopy, IR and NMR.

Preparation of Biocatalyst: to Prepare the Biocatalyst, the Mutants were Inoculated in MSM supplemented with glycerol as carbon source and naphthalene as inducer and incubated in a orbital shaker at 20°C.-60 degree C. preferentially 30-40 degree C. and 200 rpm for 12-24 hours until reaching the late expontial growth phase ($2\times10^9$ cells/ml). Subsequently the cells were harvested by centrifugation at 8000 rpm for 15 min at 4 degree C. The centrifuged cells constituting the biocatalyst, which can be used as such directly or can be immobilized on suitable matrix like calcium alginate, agrarose and polyacrylamide. Immobilized cell masses are prepared by aggregation, adsorption, or entrapment by means known in the art and have the advantage that they can be more easily separated from the water phase. The cellular extract of the cells may be obtained by sonication. The cellular remains are discarded by centrifugation, the supernatant is used as enzymatic extract.

Although living microorganisms (e.g., a culture) can be used as the biocatalyst herein, this is not required. In certain suitable microorganisms, including, the enzyme responsible for oxidation of organonitogen, organosulfur and aromatics is present on the exterior surface (the cell envelope) of the intact microorganism. Thus, non-viable (e.g., heat-killed) microorganisms can be used as a carrier for an enzyme biocatalyst. Other biocatalytic enzyme preparations that are useful in the present invention include microbial lysates, extracts, fractions, subfractions, or purified products obtained by conventional means and capable of carrying out the desired biocatalytic function. Generally, such enzyme preparations are substantially free of intact microbial cells. Enzyme biocatalyst preparations suitable for use herein can optionally be affixed to a solid support, e.g., a membrane, filter, polymeric resin, glass particles or beads, or ceramic particles or beads. The use of immobilized enzyme preparations facilitates the separation of the biocatalyst from the treated fossil fuel.

Additionally, other microbiological biocatalyst, which meets the objectives of the invention, can be employed whether now known or which will be later developed.

Concentration of Biocatalyst during the Bioconversion: The relative amounts of biocatalyst preparation and liquid fossil fuel can be adjusted to suit particular conditions, or to produce a particular level of residual sulfur, nitrogen and aromatics in the treated fossil fuel. The amount of biocatalyst preparation to be combined with a given quantity of liquid fossil fuel will reflect the nature, concentration and specific activity of the particular biocatalyst used, as well as the nature and relative abundance of inorganic and organic sulfur compounds present in the substrate fossil fuel and the degree of deep desulfurization/denitrogenation/dearomatization sought or considered acceptable.

The concentration of a particular biocatalyst can be adjusted as desired for use in particular circumstances. The biocatalyst can be diluted with additional medium or another suitable buffer, or microbial cells present in the culture can be retrieved e.g., by centrifugation, and resuspended at a greater concentration than that of the original culture. The concentrations of non-viable microorganism and of enzyme biocatalyst preparations can be adjusted similarly. In this manner, appropriate volumes of biocatalyst preparations having predetermined specific activities and/or concentrations can be obtained.

The volume and relative concentration of a given biocatalyst preparation needed for treatment is also related to the nature and identity of the substrate fossil fuel. Substrates that are very high in sulfur-bearing heterocycles, nitrogen bearing heterocycles and aromatics or for which a very low level of residual sulfur is sought will require treatment by biocatalysts of high specific activity and/or high concentration.

It is preferable to minimize the degree to which the substrate must be diluted with the biocatalyst; thus, smaller volumes of higher concentration and/or specific activity biocatalyst preparations are preferred. As a general rule, it is preferable that the biocatalyst preparation not exceed one-tenth of the volume of the combined biocatalyst and liquid fossil fuel during treatment.

In some embodiments, the biocatalyst is added in substantially non-aqueous or solid form. For example, non-aqueous formulations of enzyme biocatalysts, or immobilized enzyme biocatalysts, can be used. Other conditions that affect the rate and extent of the treatment according to the present invention include the physical conditions to which the substrate fossil fuel/biocatalyst preparation mixture is exposed.

The mixture can be incubated at any temperature between the pour point of the liquid fossil fuel and the temperature at which the biocatalytic agent is inactivated. Preferably, biocatalytic desulfurization is carried out at a temperature between about 10° C. and about 60° C. If desired, the mixture can be subjected to mechanical agitation to accelerate the rate of oxidation by ensuring thorough and even distribution of the biocatalyst preparation in the substrate. Suitable means for introducing mechanical agitation include, for example, incubation in a stirred-tank reactor.

Alternatively, the substrate fossil fuel can be caused to flow through or over a filter, membrane or other solid support to which an immobilized biocatalyst preparation is affixed.

The mixture of biocatalyst and substrate fossil fuel can be incubated for a predetermined period of time, a sufficient period of time for the desired level of oxidation to be attained. Following treatment, the biocatalyst is separated from the treated fossil fuel using known techniques such as decanting, water extraction or fractional distillation. Immobilized biocatalysts are particularly well-suited for separation from the treated fossil fuel.

Enzyme biocatalysts immobilized on a resin or on beads can be recovered by centrifugation, and enzymes affixed to membranes or filters can be recovered, e.g., by filtering the treated fossil fuel there through.

The biocatalyst described herein the present invention can be used to oxidize the aromatics and heterocyclic aromatics in one stage or in multiple stages. In multiple stages the treatment can be carried out in immediate succession, or with an interval of time between the stages of treatment. In the multistage treatment can be carried out applying same or different biocatalyst in all stages or their combinations. A significant advantage of the multistage treatment is that the result is accomplished by the removal of sulfur from a large and diverse array of the forms in which sulfur occurs in liquid fossil fuels utilizing substrate utilization of metabolic diversity of biocatalyst. Thus, the stages of desulfurization treatment in the present invention combine synergistically to produce a deeply desulfurized fuel product.

According to the present invention, bioconversion is conducted in any suitable reaction vessel by maintaining contact between the biocatalyst and the hydrocarbon for a time and under conditions effective to transform sulfur, organonitrogen and aromatic content of hydrocarbon. Contact of the bitumen with the biocatalyst is made at conditions effective for the reaction and will, like the supply of nutrients, pH adjustment, temperature, aeration, and the like, depend on the particular biocatalyst employed.

The biochemical reactions conditions preferred according to the preferred embodiments of the invention include: a temperature from 9 degree C. to 90 degree C., preferably in the range of 30-60 degree C.; an air pressure less than or equal to 150 psi and preferably from 15 psi-150 psi; a reaction time from 3 hours to 72 hours depending on the severity of the desired treatment and under aerobic conditions.

The bioconversion according to the present invention occurs during a reaction time 2-24 h at a temperature 5-50° C. and at an air pressure from 5 psi-160 psi.

According to the present invention, the biocatalyst used is at 5-20% w/v, preferentially 10-15%.

The biotreated oil thus obtained according to the current invention was recovered by centrifugation or any other process of phase separation.

According to the present invention, the oxidized or ring opened metabolites are extracted with suitable solvent resulting in treated oil having decreased aromaticity and reduced sulfur and nitrogen content. The extracted stream of polar oxidized and ring cleavage products can be subjected to chemical hydrogenation under milder conditions.

According to the present invention, in the second stage after separating biotreated fuel, it is subjected to liquid-liquid extraction solvent.

As disclosed herein, solvents used for the extraction are preferably chosen from the group consisting of N-methylpyrrolidone, furfural, by choosing extracted using polar solvents like N-methylpyrrolidone, furfural, N,N-dimethylformamide, acetonitrile, methanol, dimethyl sulphoxide individually and/or combinations thereof. Typically they are polar organic materials with low solubility in the fuel and high affinity for the polar oxidized species. They should have low affinity for other compounds typically found in the fuels. Other important properties include high density to facilitate gravity separation.

According to the present invention extraction can be carried out at any combination of temperature and pressure where both the solvent and the treated hydrocarbon mixture are liquids. Solvent can be chosen from the group consisting of, but not restricted to, water, N-methylpyrrolidone, furfural, N,N-dimethylformamide, acetonitrile, methanol, dimethyl sulphoxide, with residence time of 2 to 60 minutes in the range of 5:1 to 50:1 preferably 10:1 to 30:1 at a temperature in the range of 20 to 80.degree. C. followed by final finishing by passing through alumina, silica, clay or by adsorption on alumina, silica to obtain ultra low sulphur hydrocarbon fuels.

The presence of water is a fundamental factor for the operation of the invention, so that the oil was treated by adding the biocatlayst in the oil and minimal salt medium (MSM) with glycerol mixture. The microorganisms or their enzymes, included in this invention, are soluble in water. The oil:water as a working range of this invention is from 30:70 to 70:30.

The conditions of the bioconversion are more advantageous compared with the conventional conversion with hydrogen, because lower pressure than those required to maintain the hydrogenation can be used. Thus, the process of biochemical conversion of this invention permits the reduction of costs of equipment and operating costs, derived from conditions at high temperatures, producing at the same time a reduction in aromatic content, sulfur content and nitrogen content and its calorific value are maintained. The extracted polar compounds may be subjected to hydrogenation or may be used as substrate for manufacturing of value added product.

The process according to the present invention provides upgradation of the feedstocks by dearomatization (reduction in aromatic content), desulphurization (reduction in sulfur content) and denitrogenation (reduction in nitrogen content) in a single step or sequentially.

This invention is further illustrated by the following examples, which are not to be construed in any way as imposing, limitation upon the scope thereof. On the contrary, it is to be clearly understood that various other embodiments, modifications, and equivalents thereof which after reading the description herein, may suggest themselves to those skilled in the art without departing from the spirit of the present invention and/or the scope of the appended claims:

EXAMPLE 1

Upgradation of the Light Cycle Oil

Isolation of Polycyclic Aromatic Hydrocarbon (PAH) Degrading Bacteria:

The nutrient media (basal salt media, BSM) used for enrichment process includes $(gl^{-1})$ 6.0 g of $Na_2HPO_4$, 3.0 g of $KH_2PO_4$, 4.0 g of $NH_4Cl$, 2.5 g yeast extract, 0.1 g of $MgSO_4$ and 2.5 ml of a trace element solution ($[mgl^{-1}]$, 23 mg of $MnCl_2.2H_2O$, 30 mg of $MnCl_4.H_2O$, 31 mg of $H_3BO_3$, 36 mg of $CoCl_2.6H_2O$, 10 mg of $CuCl_2.2H_2O$, 20 mg of $NiCl_2.6H_2O$, 30 mg of $Na_2MoO_4.2H_2O$, and 50 mg $ZnCl_2$) (pH 7.0). Highly aromatic waste (2%, $wv^{-1}$) was used as carbon source and incubated at 30° C. on a rotary shaker (200 rpm) for 4 days. After four days 1 ml of the culture was transferred to fresh media containing crude oil (2%, $wv^{-1}$) and re-incubated for another four days. Following five cycles of such enrichment, 1 ml of the culture was diluted and plated on BSM agar plates containing crude oil as sole carbon source. The bacterial colonies obtained were further purified by streaking on Luria-Bertani agar. The ability of the isolates to various PAHs and highly aromatic was determined by growing it, separately, in BSM containing one of the test hydrocarbon as sole carbon source. The fastest growing strain *P. putida* IOC5a1 with ability to grow on wide range of hydrocarbon was selected for further studied for Quantitative degradation of representative PAHs. These bacterial strains were identified by 16S r RNA partial gene sequencing and biochemical assays.

Development of Biocatalyst:

The strain *P. putida* IOC5a1 was modified by transposon mediated Tn5 mutagenesis. *E. coli* C600(pGS9::Tn5) (REF) and *P. putida* IOC5a1 were grown to an $OD_{600}$ of 0.8. Transconjugants were selected on plates containing kanamycin (50 µl/ml). Colonies were picked and replica plated on BSM_Agar DBT plate to screen the mutants capable of accumulating ring-opening metabolites. This assay is based on ability of mutants to utilize various intermediate compounds of dioxygenase and salicylate pathway in agar plate. The ability of mutants to accumulate ring opened metabilites was studied using dibenzothiophene as substrate because (in contrast to other PAH) its ring cleavage products are highly colored giving a rapid visual indication of substrate transformation.

The product formed by mutants were confirmed by UV-spectrascopy, IR, and NMR. To treat mutant was grown overnight in nutrient broth and harvested by centrifugation at 8000 rpm. This pallet was used as biocatalyst. To normalize the dosing dry weight of a part of the pallet was taken by the conventional oven drying.

*Pseudomonas putida* IOC5a1 was deposited under the terms of the Budapest Treaty on the International Recognition of the Deposit of Microorganisms for the Purposes of Patent Procedure on Dec. 17, 2007 and was accepted for deposit at MTCC-IDA under the Budapest Treaty as MTCC No. 5385. As required by 37 C.F.R. 1.808 all restrictions imposed by the depositor on the availability to the public of the deposited biological material will be irrevocably removed upon granting of a patent on the present application.

LCO Treatment:

The LCO upgrading was carried out in 7 lit bioreactor containing 2.5 lit of LCO (Total aromatics: 70%, Total sulfur: 2.6%, Total Nitrogen: 240 ppm) and 1.5 lit of BSM media containing glycerol (6%) as carbon source. The dosing rate of pre-grown biocatalyst was 20 g (dry weight). The bioreactor running conditions were: Stirrer speed: 700, pH 7.0, Air: 2Liter/min. After 10 hours the cells, oil and water was separated by centrifugation at 8000 rpm, 5 min. A control without biocatalyst was run under similar experimental conditions. The treated oil was extracted with equal volume of Furfural by mixing it with solvent under stirring conditions at 60° C. for 2 hr. After extraction the oil was analyzed for aromatic content, sulfur content and nitrogen content by NMR, GC-SCD and NS analyzer (ASTM 4629) processes, respectively.

TABLE 1

Upgrading of light cycle oil

| Sample | Sulfur Content (%) | Nitrogen content (ppm) | Total Aromatic content (%) |
|---|---|---|---|
| Untreated | 2.6 | 240 | 78 |
| Treated and extracted | 0.2 | 075 | 35 |
| Untreated extracted | 2.0 | 200 | 65 |

EXAMPLE 2

Upgrading of Light Gas Oil (LGO)

The LGO was treated with the biocatalyst described above under similar experimental conditions. Results are as follows:

TABLE 2

Upgrading of LGO

| Sample | Sulfur Content (%) | Nitrogen content (ppm) | Total Aromatic content (%) |
|---|---|---|---|
| Untreated | 1.7 | 190 | 69 |
| Treated and extracted | 0.3 | 060 | 32 |
| Untreated extracted | 1.4 | 200 | 58 |

While this invention has been described in detail with reference to certain preferred embodiments, it should be appreciated that the present invention is not limited to those precise embodiments rather, in view of the present disclosure, which describes the current best mode for practicing the invention, many modifications and variations, would present themselves to those skilled in the art without departing from the scope and spirit of this invention.

We claim:

1. A process for upgrading a liquid hydrocarbon fuel by reducing an aromatic content, a sulfur content and a nitrogen content of the fuel, the process comprising:
   b. contacting a biocatalyst comprising a *P. putida* IOC5a1 (MTCC No. 5385) microbe modified via transposon-mediated Tn5 mutagenisis with the liquid hydrocarbon fuel in an aqueous medium to transform at least one of an aromatic-containing compound, a sulfur compound, and a nitrogen containing compound present in the liquid hydrocarbon fuel to polar substances;
   c. subjecting the resultant mixture of the biocatalyst and the liquid hydrocarbon fuel to a process of bioconversion; then
   d. removing the polar substances by liquid-liquid extraction with a polar solvent to obtain a dearomatized, desulphurised and denitrogenated liquid hydrocarbon fuel; and
   e. recovering an upgraded liquid hydrocarbon fuel.

2. The process as claimed in claim 1, wherein the biocatalyst is capable of transforming any of aromatics, polycyclic aromatics, organosulfur compounds, and organonitrogen compounds to polar compounds without transforming aliphatic hydrocarbons in the liquid hydrocarbon fuel.

3. The process as claimed in claim 1, wherein the liquid hydrocarbon fuel is treated with biocatalyst in a single step or sequentially.

4. The process according to claim 3, wherein the liquid hydrocarbon fuel is treated sequentially with same or different biocatalyst.

5. The process as claimed in claim 1, wherein the polar solvent is selected from a group consisting of N-methylpyrrolidone, furfural, N,N-dimethylformamide, acetonitrile, methanol, dimethyl sulphoxide individually and combinations thereof.

6. The process as claimed in claim 1, wherein the biocatalyst is recovered and employed in at least one additional stage.

7. The process as claimed in claim 1, wherein the bioconversion occurs at a temperature between 5-50° C.

8. The process as claimed in claim 1, wherein the bioconversion occurs after incubation for about 2-24 h.

9. The process as claimed in claim 1, wherein the biocatalyst is employed at 5-20% w (dry weight)/v of the mixture.

10. The process as claimed in claim 1, wherein the bioconversion occurs at an air pressure from 5psi-160 psi.

11. The process as claimed in claim 1, wherein the bioconverted liquid hydrocarbon fuel is separated from the polar substances by oil-water separation process.

12. The process as claimed in claim 1, wherein the liquid hydrocarbon fuel is an organic material selected from a group consisting of single ring aromatic compound, a multi-ring aromatic compound, an alkylaromatic compound, a heteroatom-containing single ring aromatic compound, a heteroatom-containing multi-ring aromatic compound, a heteroatom-containing alkylaromatic compound, a crude oil, a petroleum refining intermediate, a refined petroleum, a petrochemical stream, a light gas oil, a light cycle oil, a vacuum gas oil, a diesel, a gasoline, a shale oil, a heavy oil, a bitumen, and a coal liquid.

13. The process as claimed in claim 1, wherein the biocatalyst is in free or immobilized form.

14. The process as claimed in claim 1, wherein the biocatalyst is employed at 10-15% w (dry weight)/v of the mixture.

\* \* \* \* \*